United States Patent

Stoltefuss

[11] 4,220,782
[45] Sep. 2, 1980

[54] PREPARATION OF 1-DESOXY-NOJIRIMICIN AND N-SUBSTITUTED DERIVATIVES

[75] Inventor: Jürgen Stoltefuss, Haan, Fed. Rep. of Germany

[73] Assignee: Bayer Aktiengesellschaft, Leverkusen, Fed. Rep. of Germany

[21] Appl. No.: 50,907

[22] Filed: Jun. 21, 1979

[30] Foreign Application Priority Data

Jul. 11, 1978 [DE] Fed. Rep. of Germany ....... 2830469

[51] Int. Cl.² .......................................... C07D 211/46
[52] U.S. Cl. ...................................... 546/242; 536/4; 536/18
[58] Field of Search ......................................... 546/242

[56] References Cited

U.S. PATENT DOCUMENTS 4,137,231  1/1979  Murai et al. .......................... 546/242

OTHER PUBLICATIONS

Ishida, N., et al., *J. Antibiotics* (Tokyo), Sera, 20, 66 (1967).
Inouye, S., et al., Tetrahedron, 23, 2125-2144 (1968).
Saeki, H., et al., *Chem Pharm. Bull.*, 16, 2477-2481 (1968).

*Primary Examiner*—John M. Ford
*Assistant Examiner*—Richard A. Schwartz
*Attorney, Agent, or Firm*—Sprung, Felfe, Horn, Lynch & Kramer

[57] ABSTRACT

The invention relates to a process for the production of a compound of the formula

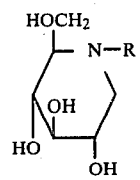

(I)

in which R denotes a hydrogen atom or an alkyl, aralkyl or aryl group and comprises deblocking a compound of the general formula

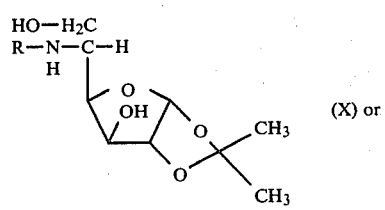

(X) or

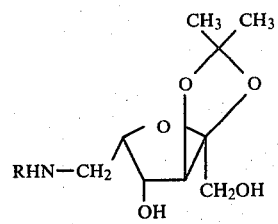

(XI)

in which R has the meaning indicated above, by treatment with a strong mineral acid and isolating the intermediate product in the form of a salt thereof and then hydrogenating said salt with a suitable hydrogen donor, or, in a one-pot process, first deblocking the starting material by treatment with a strong mineral acid and, after controlled addition of a base, hydrogenating directly.

9 Claims, No Drawings

PREPARATION OF 1-DESOXY-NOJIRIMICIN AND N-SUBSTITUTED DERIVATIVES

The present invention relates to a new, chemically unobvious process for the production of a compound of the general formula

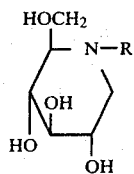

in which R denotes a hydrogen atom or an alkyl, aralkyl or aryl group.

It has already been disclosed that the compound known by the name 1-desoxy-nojirimicin, of the formula (I; R=H), can be obtained either by extraction from plants of the morus species according to German Offenlegungsscrift (German Published Specification) No. 2,656,602, or microbiologically with the aid of organisms of the Bacillaceae family, in particular of the DSM 7 strain, according to German Offenlegungsscrhift (German Published Specification) No. 2,658,563. The compounds of the formula (I) can be used as agent for the treatment of diabetes, hyperlipaemia and adiposity.

It has also already been disclosed that 1-desoxy-nojirimicin can be prepared by hydrogenating the free bases (II) or (III)

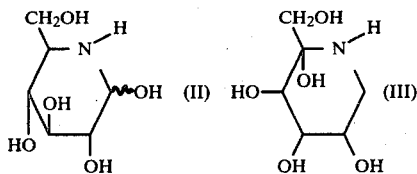

which are not very stable, according to H. Saki and E. Ohki, Chem. Pharm. Bull. 16, 2477 to 2481 (1968) and H. Paulsen, I. Sangster and H. Heyns, Chem. Ber. 100, 802 to 815 (1967).

The compound (II) thereby used as a starting material is prepared either by a process in which 5-amino-5-desoxy-1,2,-O-isopropylidene-α-D-glucofuranose (IV) is converted, by passing sulphur dioxide in for 60 hours, into a stable bisulphite adduct (V), which then gives II by treatment with barium hydroxide

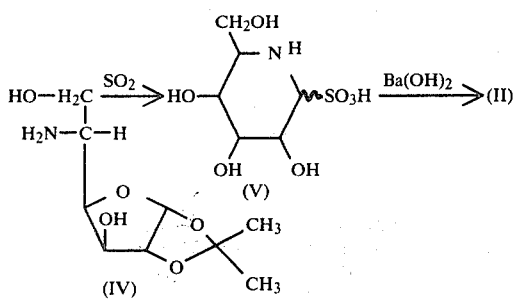

(German Auslegeschrift (German Published Specification) No. 1,768,044), or by a process in which the compound IV is converted into the trifluoroacetylated derivative VI, which gives the trifluoroacetyl derivative VII by boiling with dilute hydrochloric acid. Subsequent splitting off of the substituents via anion exchangers gives (II)

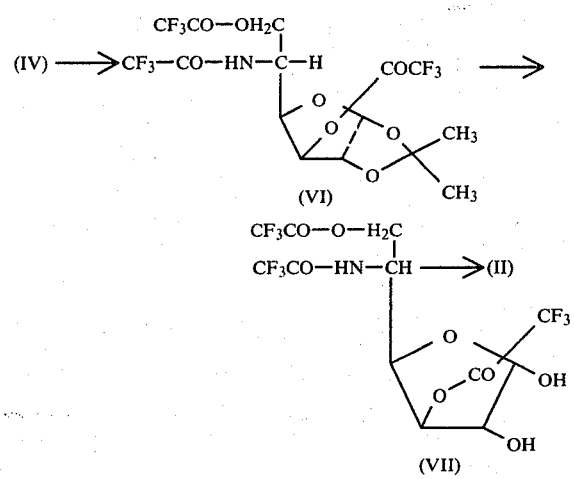

or the compound (II) is prepared microbiologically (U.S. Patent No. 3,998,698).

The compound (III) is obtained from 6-amino-2,3-O-isopropylidene-6-desoxy-α-L-sorbofuranose VIII by splitting, and subsequent liberation of the resulting hydrochloride IX by chromatography over an anion exchanger.

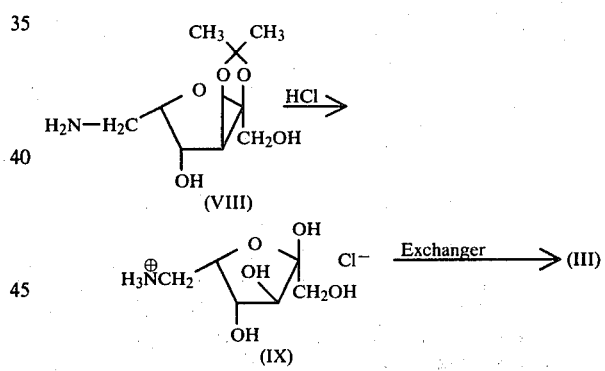

The processes listed here for the preparation of 1-desoxy-nojirimicin all proceed via several time-consuming stages, and passing through the unstable compounds II and III as intermediate products must unavoidably lead to by-products.

Furthermore, the processes known hitherto for the preparation of the compoun I (R=H) in each case require expensive purification steps, such as extraction, column chromatography or chromatography on exchangers, which in some cases are also necessary because the hydrogenation of the free bases does not proceed stereospecifically.

It has now been found, surprisingly, that according to the present invention the compounds of formula (I) are obtained in excellent yields when a compound of the general formula (X) or (XI).

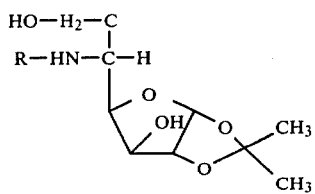
(X)

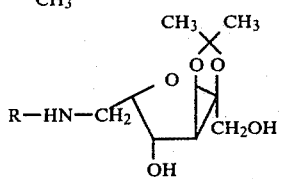
(XI)

in which R has the meaning indicated above, is deblocked by treatment with a strong mineral acid to give an ammonium salt of the probable structure XII or XIII

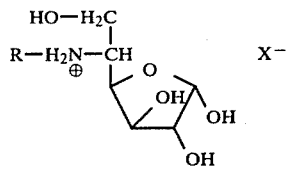
(XII)

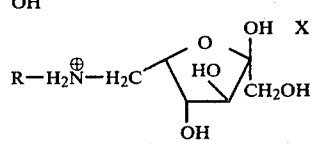
(XIII)

and the salt is then either isolated and hydrogenated with a suitable hydrogen donor, or, in a one-pot process, the compound of formula (X) or (XI) is first deblocked by treatment with a strong mineral acid and, after controlled addition of a base, the product is hydrogenated directly. Furthermore, hydrogenation of the salt of formula (XIII) gives, in a reaction which proceeds stereo-specifically, only the desired gluco-compounds.

It is to be described as exceptionally surprising that the compounds of formula (I) are obtained in excellent yields and as stereospecifically pure compounds by the reaction according to the invention, because according to the state of the art it had to be expected that the deblocking of the compounds of formula (X) with mineral acids would only lead to pyridine derivatives and that the hydrogenation of the free bases obtained by deblocking compounds of formula (XI) would lead to mixtures of gluco-compounds and ido-compounds (see Paulsen, Sangster and Heyns, supra.)

R preferably denotes hydrogen, alkyl with 1 to 30, in particular 1 to 18, carbon atoms or optionally substituted phenyl, phenyl-$C_1$ to $C_4$ alkyl or naphthyl-$C_1$ to $C_6$ alkyl, possible substituents of phenyl and naphthyl being (preferably 1 to 3 particularly 1 or 2) halogen, in particular F, Cl or Br, $C_1$ to $C_4$ alkyl, $C_1$ to $C_4$ alkoxy, nitro, amino or cyano.

In very particularly preferred compounds of the formula I, R denotes hydrogen, $C_1$ to $C_{12}$ alkyl, in particular $C_1$ to $C_4$ alkyl, or phenyl.

The compounds of the formulae X and XI used as starting materials can be prepared by methods which are in themselves known, for example by subjecting 3-O-benzyl-6-O-triphenylmethyl-1,2-O-isopropylidene-α-D-xylo-hexofuranose-5-ulose to reductive amination and then splitting off the trityl and benzyl group with sodium in liquid ammonia

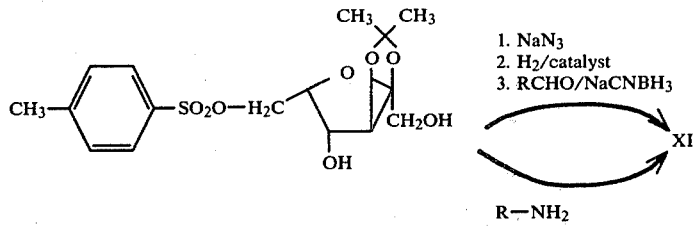

or, for example, by reacting 2,3-O-isopropylidene-6O-p-toluenesulphonyl-α-L-sorbofuranose with sodium azide, subsequently hydrogenating the product and if necessary subjecting it to reductive alkylation; or reacting the starting material directly with amines.

If, for example, 6-amino-2,3,O-isopropylidene-6-desoxy-α-L-sorbofuranose is used as the starting material and hydrochloric acid is used as the acid, the course of the reaction can be represented by the equation which follows:

If 1,2-O-isopropylidene-5-methylamino-5-desoxy-α-D-glucofuranose is used as the starting material, the course of the reaction can be formulated as follows:

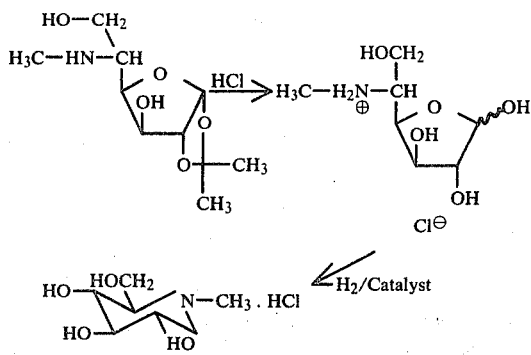

The free compounds can easily be prepared from the salts thereby formed, by adding suitable inorganic or organic bases or by neutralisation with anion exchangers.

The acids used in the process according to the invention are strong mineral acids, such as hydrochloric acid or sulphuric acid and hydrochloric acid is preferably used, it being possible to vary the concentration for splitting off the isopropylidene group within a wide range, 2 N to 10 N hydrochloric acid preferably being used.

It is an essential part of this invention that the acid concentration before the hydrogenation is decreased by adding inorganic or organic bases, e.g. NaOH, KOH, morpholine, tributylamine, N-methyl piperidine or picoline, preferably triethylamine or pyridine.

The compound of formula (I) is obtained in high purity and particularly high yield if 1 to 1.2 equivalents of acid are present in the hydrogenation step for one mol of compound to be hydrogenated.

Possible diluents are water, lower alcohols and other protic solvents, but preferably water.

The hydrogenation according to the invention is carried out either in the presence of catalysts, or by other suitable hydrogen donors. Possible catalysts are those which are generally used for hydrogenation reactions, such as Raney nickel, platinum dioxide, palladium-on-charcoal and the like; examples of other suitable hydrogen donors are sodium borohydride or sodium cyanoborohydride.

The reaction temperatures for both the above-mentioned reaction stages can be varied within a wide range. In general, the reaction is carried out between 0° and about 150° C. preferably between 20° and 100° C.

The reaction can be carried out either under normal pressure or at elevated pressure in both the abovementioned reaction stages. In general, the reaction is carried out under pressures between 1 and 150 bars.

The preparation of compounds of the present invention will now be illustrated by the following Examples.

EXAMPLE 1

A solution of 2 g of 5-amino-5-desoxy-1,2-O-isopropylidene-α-D-glucofuranose in 8 ml of 2 N hydrochloric acid is stirred for 24 hours. It is diluted with 5 ml of water and, after adding 0.69 g of triethylamine and 0.3 g of Raney nickel, hydrogenation is carried out under 3.5 bars for 5 hours. The catalyst is filtered off and concentrated in vacuo and the residue is twice re-concentrated in the presence of ethanol, whereupon crystallisation starts. The crystals are stirred with ethanol, filtered off and washed thoroughly with ethanol. 1.45 g (79.7% of theory) of 1-desoxy-norjirimicin hydrochloride of melting point 209° to 210° C., with decomposition, are obtained.

EXAMPLE 2

(a) 100 g of 6-amino-6-desoxy-1,2-O-isopropylidene-L-sorbofuranose are dissolved in 120 ml of 8 N hydrochloric acid under cooling. After 2 hours stirring seed crystals of the final product are added and stirring is continued for one hour. 600 ml of ethanol are added, the product is filtered off after 3 hours cooling to 0° C. and washed with ethanol. 73.4 g of 6-amino-6-desoxy-L-sorbofuranose-hydrochlorid-monohydrate are obtained.

(b) 2 g of 6-amino-6-desoxy-L-sorbofuranose hydrochloride monohydrate are dissolved in 10 ml of water and hydrogenation is carried out with 0.2 g of platinum dioxide under 3.5 bars for 2 hours. The catalyst is filtered off, the filtrate is concentrated, the residue is twice re-concentrated in the presence of methanol and the resulting crystals are stirred with methanol and filtered off. 1.3 g (76% of theory) of 1-desoxy-nojirimicin hydrochloride of melting point 210° C., with decomposition, are obtained.

EXAMPLE 3

500 mg (2.5 mols) of 1-desoxy-nojirimicin hydrochloride are suspended in 2 ml of dimethylformamide. 0.7 ml (5 mmols) of triethylamine is then added, whilst stirring, and after this 5 ml of ethanol. After 30 minutes, the solid is filtered off and washed thoroughly with ethanol.

385 mg (95% of theory) of chloride-free 1-desoxy-nojirimicin of melting point 196° C. are obtained.

EXAMPLE 4

N-Phenyl-1-desoxy norjirimicin 150 mg of 6-phenylamino-2,3,-O-isopropylidene-6-desoxy-α-L-sorbofuranose are dissolved in 1.0 ml of 6 N HCl and the solution is left to stand at 0° C. for 18 hours. It is diluted with 3 ml of water, 0.755 ml of triethylamine are added and hydrogenation is carried out under 3 bars of $H_2$ with Raney nickel as the catalyst for 3 hours. Filtration of the catalyst and rinsing with water are effected, the product phase is treated with an anion exchanger (OH⊖ form), the exchanger is filtered off and the filtrate is concentrated. The resulting evaporation residue is investigated by mass spectroscopy. The following mass peaks, inter alia, are obtained: m/e 239 (molecular peak), m/e 208 (M-$CH_2OH$) and m/e 148 (M-$CH_2OH$-2CHOH).

EXAMPLE 5

A solution of 1 g of 5-methylamino-5-desoxy-1,2-O-isopropylidene-α-D-glucofuranose of melting point 127° C., in 4 ml of 6 N HCl is left to stand at 0° C. for 18 hours and diluted with water to about 10 ml, 2.76 ml of triethylamine are added and hydrogenation is carried out with 0.2 g of platinum oxide under 3.5 bars of $H_2$ for 3 hours. Filtration and washing with water are effected. The aqueous solution is discharged onto a column filled with a cation exchanger (H⊖ form) and eluted with 1% strength aqueous ammonia. The eluate is concentrated and the residue is twice taken up with ethanol and concentrated. On cooling, the desired compound crystallises out. It is stirred with methanol, filtered off and washed with methanol. 420 mg of N-methyl-1-desoxynojirimicin of melting point 152° C. are obtained.

What is claimed is:

1. A process for the production of 1-desoxy-nojirimicin or an N-substituted derivative thereof, of the formula

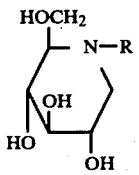

in which R denotes a hydrogen atom or an alkyl, aralkyl or aryl group, which comprises deblocking a compound of the general formula

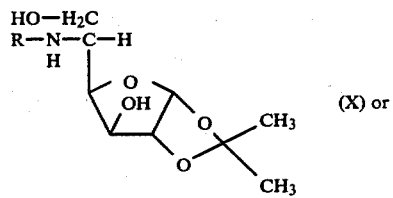

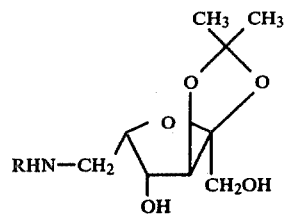

in which R has the meaning indicated above, by treatment with a strong mineral acid and isolating the intermediate product in the form of a salt thereof and then hydrogenating said salt with a suitable hydrogen donor, or, in a one-pot process, first deblocking the starting material by treatment with a strong mineral acid at a normality adequate to preclude the formation of a pyridine compound and, after controlled addition of a base, hydrogenating directly.

2. A process according to claim 1, in which the deblocking is carried out with hydrochloric acid.

3. A process according to claim 2, in which 2 N to 10 N hydrochloric acid is used.

4. A process according to claim 1 or 2 in which 1 to 1.2 equivalents of acid are used per mol of compound of formula (X) or (XI) during the hydrogenation step.

5. A process according to claim 1 or 2, in which the deblocked intermediate product is hydrogenated in the form of its salts.

6. A process according to claim 1, in which the process is carried out at 0° to 150° C. and under 1 to 150 bars.

7. A process according to claim 6 in which the process is carried out at a temperature between 20° and 100° C.

8. A process according to claim 1, in which R denotes a hydrogen atom, an alkyl group with 1 to 30 carbon atoms, or an optionally substituted phenyl, phenyl-$C_1$ to $C_4$ alkyl or naphthyl-$C_1$ to $C_6$ alkyl.

9. A process according to claim 8, in which R denotes a hydrogen atom, a $C_1$ to $C_4$ alkyl group or a phenyl radical.

* * * * *